(12) United States Patent
Shinfeld et al.

(10) Patent No.: US 11,547,525 B2
(45) Date of Patent: Jan. 10, 2023

(54) ENDOTRACHEAL TUBE CLEANING DEVICE SYSTEM AND METHOD

(71) Applicants: THE MEDICAL RESEARCH INFRASTRUCTURE AND HEALTH SERVICES FUND OF THE TEL AVIV MEDICAL CENTER, Tel Aviv (IL); TEL HASHOMER MEDICAL RESEARCH INFRASTRUCTURE AND SERVICES LTD., Ramat Gan (IL)

(72) Inventors: Amihay Shinfeld, Givataim (IL); Yoav Paz, Tel Aviv (IL); Emanuel Mendes, Petach-Tikva (IL); Joseph Feldman, Tel Aviv (IL)

(73) Assignees: TEL HASHOMER MEDICAL RESEARCH INFRASTRUCTURE AND SERVICES LTD., Ramat Gan (IL); THE MEDICAL RESEARCH INFRASTRUCTURE AND HEALTH SERVICES FUND OF THE TEL AVIV MEDICAL CENTER, Tel Aviv (IL)

( * ) Notice: Subject to any disclaimer, the term of this patent is extended or adjusted under 35 U.S.C. 154(b) by 0 days.

(21) Appl. No.: 16/972,601

(22) PCT Filed: Jun. 6, 2019

(86) PCT No.: PCT/IL2019/050652
§ 371 (c)(1),
(2) Date: Dec. 6, 2020

(87) PCT Pub. No.: WO2019/234749
PCT Pub. Date: Dec. 12, 2019

(65) Prior Publication Data
US 2021/0113298 A1    Apr. 22, 2021

Related U.S. Application Data

(60) Provisional application No. 62/681,420, filed on Jun. 6, 2018.

(51) Int. Cl.
*A61B 90/70*   (2016.01)
*A61M 25/00*   (2006.01)
(Continued)

(52) U.S. Cl.
CPC .............. *A61B 90/70* (2016.02); *A61M 16/04* (2013.01); *A61M 25/00* (2013.01); *B08B 9/0436* (2013.01);
(Continued)

(58) Field of Classification Search
CPC .............. B08B 9/0436; B08B 2209/04; A61B 2090/701; A61M 2025/0019; A61M 2209/10
(Continued)

(56) References Cited

U.S. PATENT DOCUMENTS

| 5,003,657 A | 4/1991 | Boiteau et al. |
| 8,601,633 B2 | 12/2013 | Vazales et al. |

(Continued)

FOREIGN PATENT DOCUMENTS

| EP | WO 2011/126812 A1 * | 10/2011 |
| EP | WO 2014/049492 A1 * | 4/2014 |

(Continued)

OTHER PUBLICATIONS

PCT International Search Report for International Application No. PCT/IL2019/050652, dated Oct. 29, 2019, 9pp.
(Continued)

*Primary Examiner* — Randall E Chin
(74) *Attorney, Agent, or Firm* — The Roy Gross Law Firm, LLC; Roy Gross

(57) ABSTRACT

An endotracheal tube cleaning device, including a rod, and a cleaning head coupled to a distal end of the rod, including a low friction-generating surface; and a high friction-generating surface, wherein the low friction-generating surface contacts an inner surface of the endotracheal tube when moved along the tube in a first direction and the high friction-generating surface contacts the inner surface of the endotracheal tube when moved in a second, opposite direction.

15 Claims, 9 Drawing Sheets

(51) Int. Cl.
*B08B 9/043* (2006.01)
*A61M 16/04* (2006.01)
(52) U.S. Cl.
CPC .............. *A61B 2090/701* (2016.02); *A61M 2025/0019* (2013.01); *A61M 2209/10* (2013.01); *B08B 2209/04* (2013.01)
(58) Field of Classification Search
USPC .......................................... 15/104.16, 104.31
See application file for complete search history.

(56) References Cited

U.S. PATENT DOCUMENTS

| | | | |
|---|---|---|---|
| 8,684,022 B1* | 4/2014 | McFarland | F24F 13/222 137/15.07 |
| 9,332,891 B2 | 5/2016 | Vazales et al. | |
| 9,445,714 B2 | 9/2016 | Vazales et al. | |
| 2009/0178681 A1 | 7/2009 | Bracken | |
| 2010/0163074 A1* | 7/2010 | Hansen | A61B 90/70 134/8 |
| 2011/0289705 A1* | 12/2011 | Asano | A61B 1/122 15/104.05 |
| 2014/0090642 A1 | 4/2014 | Bagwell et al. | |
| 2014/0378792 A1 | 12/2014 | Krimsky et al. | |
| 2015/0136123 A1 | 5/2015 | Donlon et al. | |
| 2015/0374942 A1 | 12/2015 | Bateman et al. | |
| 2017/0065367 A1 | 3/2017 | Vazales et al. | |
| 2018/0249903 A1 | 9/2018 | Strombergsson et al. | |

FOREIGN PATENT DOCUMENTS

| | | |
|---|---|---|
| EP | 2397066 B1 | 9/2015 |
| EP | 2900307 B1 | 6/2017 |
| WO | 1989000058 A1 | 1/1989 |
| WO | 2007002990 A1 | 1/2007 |
| WO | 2011126812 A1 | 10/2011 |

OTHER PUBLICATIONS

PCT Written Opinion for International Application No. PCT/IL2019/050652, dated Oct. 29, 2019, 8pp.
PCT International Preliminary Report on Patentability for International Application No. PCT/IL2019/050652, dated Dec. 8, 2020, 9pp.

* cited by examiner

SECTION A-A

ENDOTRACHEAL TUBE CLEANING DEVICE SYSTEM AND METHOD

CROSS REFERENCE TO RELATED APPLICATIONS

This application is a National Phase of PCT Patent Application No. PCT/IL2019/050652 having International filing date of Jun. 6, 2019 entitled "ENDOTRACHEAL TUBE CLEANING DEVICE, SYSTEM AND METHOD", which claims the benefit of priority from U.S. Provisional Patent Application No. 62/681,420 filed on Jun. 6, 2018 entitled "ENDOTRACHEAL TUBE CLEANING SYSTEM AND METHOD." The contents of the above applications are all incorporated by reference as if fully set forth herein in their entirety.

FIELD OF THE INVENTION

The present invention, in some embodiments thereof, relates to tube cleaning systems and methods and, more particularly, but not exclusively, to an endotracheal tube cleaning system and method.

BACKGROUND

An Endotracheal tube is used to provide a clear airway through the mouth, pharynx and trachea or nose, nasopharynx and trachea into the tracheobronchial tree of patients. Endotracheal tubes are used to support life during and after major surgery, trauma, or the development of certain severe tracheal conditions, such as pneumonia and sepsis and most cases of respiratory failure.

Ventilator-associated pneumonia is a common complication in patients receiving mechanical ventilation and is an important cause of increased mortality, length of hospital stay, and cost. After several days of intubation and mechanical ventilation, the lumen of an endotracheal tube becomes heavily colonized by bacteria, which often organizes into a thick, mature biofilm. The formation of endotracheal tube biofilms and subsequent, recurrent transfer of bacteria to the lower respiratory tract may lead to the development of lower respiratory tract infection and ventilator-associated pneumonia.

U.S. Pat. No. 8,601,633, describes a cleaning device that removes the biofilm accumulated on the interior surface of the tube. The device comprises a cleaning element, which can change its geometry to fit the tube by being inflatable or by being collapsible/expandable.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools, kits, and methods which are meant to be exemplary and illustrative, not limiting in scope.

According to an aspect of some embodiments of the present invention, there is provided an endotracheal tube cleaning device, including a rod, and a cleaning head coupled to a distal end of the rod, including a low friction-generating surface, and a high friction-generating surface. In some embodiments, the low friction-generating surface contacts an inner surface of the endotracheal tube when moved along the tube in a first direction, and the high friction-generating surface contacts the inner surface of the endotracheal tube when moved in a second, opposite direction.

According to some embodiments, the high friction-generating surface includes a pliable edge, and movement of the head within the endotracheal tube in a distal direction flexes the pliable edge proximally bringing the low friction-generating surface to glide along an inner surface of the endotracheal tube. In some embodiments, movement of the head within the endotracheal tube in a proximal direction flexes at least the pliable edge distally bringing the high friction-generating surface to rub against the inner surface of the endotracheal tube thereby cleaning the inner surface.

According to some embodiments, the high friction-generating cleaning surface is textured and the low friction generating surface is smooth. In some embodiments, a surface area of the low friction generating cleaning surface is smaller than a surface area of the high friction generating surface. In some embodiments, the low friction generating surface is located distally to the high friction-generating cleaning surface. In some embodiments, the low friction generating surface has a smaller diameter than the diameter of the inner surface of the endotracheal tube defining a gap between an edge of the low friction generating surface and the inner surface sized to accommodate at least a thickness of the low friction generating surface.

According to some embodiments, the cleaning device is configured to be stowed in the endotracheal tube in between cleanings, at least prior to insertion of the endotracheal tube into a subject or immediately following a previous cleaning of the endotracheal tube. In some embodiments, the cleaning device includes an insertion limiter coupled to a proximal end of the rod. In some embodiments, the cleaning device is configured to remain in the endotracheal tube in between cleanings, in a maximally inserted state in which at least the rod is disposed within the endotracheal tube, the cleaning head in a fully inserted state extends beyond a distal rim of the endotracheal tube, and the insertion limiter engages a proximal rim of the endotracheal tube and blocks further insertion of the device into the tube.

According to some embodiments, at the fully extended state, the head is configured to be disposed in a lumen of the pulmonary bronchi between the bronchi carina and the distal rim of the endotracheal tube. In some embodiments, the cleaning head includes a proximal high friction-generating cleaning surface, and wherein at a maximally inserted state, the high friction-generating cleaning surface faces the distal rim of the tube and a gap is defined between the high friction-generating cleaning surface and the distal rim of the tube. In some embodiments, the cleaning device includes a distal end, and wherein at the maximally inserted state, a gap is defined between a distal end of the cleaning device and patient tissues.

According to some embodiments, the diameter of the high friction-generating cleaning surface is equal or larger than the diameter of the inside surface of the endotracheal tube. In some embodiments, the diameter of the high friction-generating cleaning surface is equal or larger than the external diameter of the endotracheal tube. In some embodiments, the high friction-generating cleaning surface is configured to flex into a distal eyelet (Murphy's Eye) of the endotracheal tube, when the cleaning head moves in a proximal direction over the eyelet, such as it rubs the surfaces of the eyelet. In some embodiments, a length of the rod is longer than a length of the endotracheal tube.

According to an aspect of some embodiments of the invention, the cleaning device includes a collector sleeve, configured to receive the cleaning head after being removed from the endotracheal tube. In some embodiments, the collector sleeve is configured to encompass the cleaning device after being removed from the endotracheal tube. In some embodiments, the collector sleeve is expandable and compressible between a compressed state and an expanded state. In some embodiments, the cleaning device includes one or more rod buffers mounted on the rod in between the distal end and the proximal end of the rod, wherein the external diameter of the buffers is smaller than the diameter of the inner wall of the tube.

According to an aspect of some embodiments of the invention there is provided an endotracheal tube cleaning device, including a rod, and a cleaning head coupled to a distal end of the rod, including a discoid base mounted on the rod, and having a diameter smaller than a diameter of an inner surface of the endotracheal tube such that a gap is defined between an edge of the discoid base and the inner surface, and a cleaning surface mounted adjacent to the discoid base and having at least a pliable edge, wherein, when moving the cleaning head in a proximal direction within the endotracheal tube, at least the pliable edge flexes distally into the gap such that the discoid base urges the high friction-generating cleaning surface against the inner surface thereby cleaning the inner surface.

In some embodiments, the elasticity of the discoid base is lower than the elasticity of the cleaning layer. In some embodiments, the high friction-generating cleaning surface is mounted proximally to the discoid base. In some embodiments, the cleaning head includes the discoid base and the pliable edge mounted to a proximal portion of the edge of the discoid base.

According to an aspect of some embodiments of the invention, there is provided an endotracheal tube cleaning system, the system includes an endotracheal tube cleaning device including a cleaning head, and a collector sleeve attachable to a proximal end of an endotracheal tube and configured to receive the cleaning head after being removed from the endotracheal tube. In some embodiments, the collector sleeve is configured to receive the cleaning device after being removed from the endotracheal tube. In some embodiments, the cleaning device is attachable to the collector sleeve.

In some embodiments, the collector sleeve is expandable and compressible between a compressed state and an expanded state. In some embodiments, cleaning of the tube is performed by retracting the cleaning device from the maximally inserted state. In some embodiments, the device includes a cleaning head, and wherein in between cleanings the cleaning device remains in a maximally inserted state in which the cleaning head is fully extended distally beyond a distal rim of the endotracheal tube.

According to an aspect of some embodiments of the invention there is provided a method for cleaning an endotracheal tube, including inserting into a clean endotracheal tube an endotracheal tube device including a rod and a cleaning head coupled to a distal end of the rod, including a high friction-generating surface having at least a pliable edge, and a low friction-generating surface, and moving the head within the endotracheal tube in a distal direction, and flexing at least the pliable edge proximally bringing the low friction-generating surface to glide along an inner surface of the endotracheal tube, followed by retracting the head within the endotracheal tube in a proximal direction, and flexing at least the pliable edge distally bringing the high friction-generating cleaning surface to rub against the inner surface of the endotracheal tube thereby cleaning the inner surface.

In some embodiments, the cleaning device includes an insertion limiter coupled to a proximal end of the rod and the method includes at least partially inserting the cleaning device into a clean endotracheal tube, inserting the endotracheal tube with the endotracheal tube cleaning device into a trachea, and inserting the cleaning device further until the insertion limiter abuts a proximal edge of the tracheal tube.

In some embodiments, the cleaning device includes a distal end, and wherein inserting the cleaning device until the insertion limiter abuts a proximal edge of the tracheal tube includes forming a gap between a distal end of the cleaning device and patient tissues. In some embodiments, moving the head within the endotracheal tube proximally and cleaning the endotracheal tube. In some embodiments, the endotracheal tube cleaning device includes a collector sleeve attachable to a proximal end of the endotracheal tube and configured to receive the cleaning head after being removed from the endotracheal tube.

In some embodiments, the method includes moving the head within the endotracheal tube proximally and into the collector sleeve and detaching and disposing of the collector sleeve and at least the head.

According to an aspect of some embodiments of the invention there is provided an endotracheal tube cleaning kit, including at least one endotracheal cleaning device including a rod, and a cleaning head coupled to a distal end of the rod, including a high friction-generating cleaning surface having at least a pliable edge, and a low friction-generating surface. In some embodiments, movement of the head within the endotracheal tube in a distal direction flexes at least the pliable edge proximally bringing the low friction-generating surface to glide along an inner surface of the endotracheal tube, and movement of the head within the endotracheal tube in a proximal direction flexes at least the pliable edge distally bringing the high friction-generating cleaning surface to rub against the inner surface of the endotracheal tube thereby cleaning the inner surface. In some embodiments, the kit includes at least one insertion limiter coupled to a proximal end of the rod, and at least one collector sleeve attachable to a proximal end of the endotracheal tube and configured to receive the cleaning head after being removed from the endotracheal tube.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1:
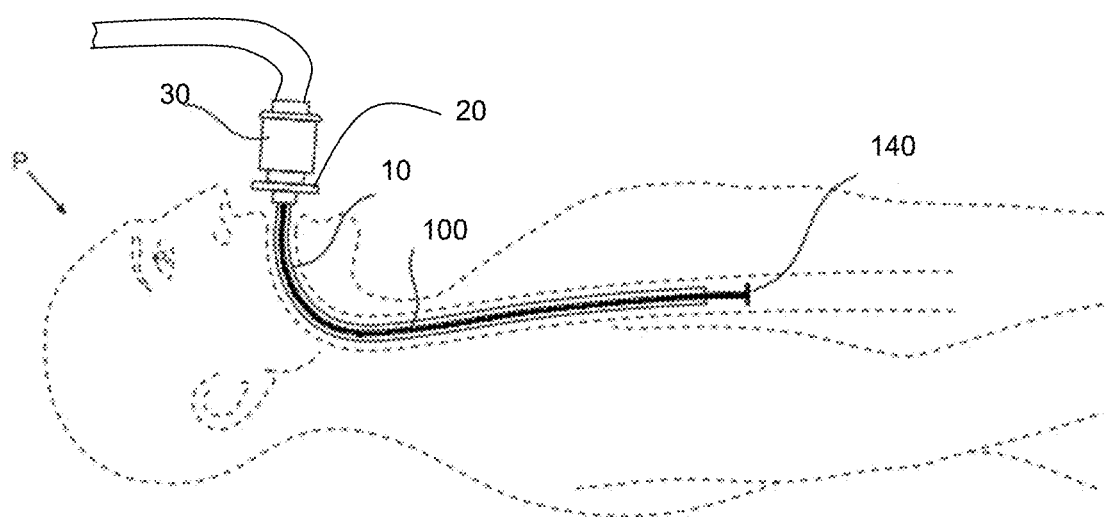
FIG. 1 is a side view simplified illustration of an endotracheal tube cleaning device implemented in an endotracheal tube according to some embodiments of the present invention.

Patients with chronic pulmonary diseases need to be supported by ventilators via endotracheal tubes for lengthy periods of time. Often, biofilm (secretions and debris) begins to accumulate on the inner surface of the endotracheal tubes shortly after initial intubation (e.g., within 24 hours). The biofilm can contain harmful bacteria (e.g., gram-negative organisms) that, if not removed in a timely and efficient manner, can be a potential nidus for infection. However, frequent removal of the endotracheal tube from the patient for cleaning is inconvenient and can be dangerous.

According to an aspect of some embodiments of the present invention, there is provided an endotracheal tube cleaning device configured to be inserted distally into an endotracheal tube and to be retracted proximally out of the tube. The cleaning device is configured to clean secretions and debris accumulated within the endotracheal tube when retracting the device out of the endotracheal tube. In some embodiments, in between cleaning of the tube, the device remains located within the tube, while concurrently maintaining a continuous airflow communication from and to the lungs throughout the endotracheal tube. In some embodiments, the device is configured to be inserted into the endotracheal tube prior to insertion of the endotracheal tube into the patient. A potential advantage in inserting the device prior to intubation of the patient is in that the device is inserted when the tracheal tube is clean and thus does not push debris accumulated on the inner surface of the endotracheal tube into the patient's body.

According to an aspect of some embodiments of the present invention, there is provided an endotracheal tube cleaning device comprising: a rod, coupled at a distal end to a cleaning head, and at a proximal end to an insertion limiter. In some embodiments of the invention, the rod comprises a distal end and a proximal end, the cleaning head is mounted at the distal end of the rod.

According to an aspect of some embodiments of the present invention, there is provided an endotracheal tube cleaning device comprising: a rod, and a cleaning head coupled to a distal end of said rod, comprising a high friction-generating cleaning surface having at least a pliable edge, and a low friction-generating surface, wherein movement of the cleaning head within the endotracheal tube in a distal direction flexes at least the pliable edge proximally bringing the low friction-generating surface to glide along an inner surface of the endotracheal tube; and movement of the cleaning head within the endotracheal tube in a proximal direction flexes at least said pliable edge distally bringing said high friction-generating cleaning surface to rub against the inner surface of said endotracheal tube thereby cleaning the inner surface of the endotracheal tube.

In some embodiments of the present invention, the high friction generating cleaning surface is textured and the low friction generating cleaning surface is smooth.

In some embodiments of the present invention, the surface area of the low friction generating cleaning surface is smaller than a surface area of said high friction generating cleaning surface.

In some embodiments of the present invention, the low friction generating cleaning surface is located distally to and has a smaller diameter than a diameter of said high-friction generating cleaning surface defining a gap between an edge of the low friction generating surface and the inner surface of the endotracheal tube. In some embodiments, the movement of the cleaning head in a proximal direction flexes at least the pliable edge, distally into the gap such that the edge of the low friction generating surface urges the high-friction generating cleaning surface against the inner surface thereby cleaning the inner surface of the endotracheal tube.

According to an aspect of some embodiments of the present invention there is provided an endotracheal tube cleaning kit, the kit comprises: an endotracheal tube cleaning device comprising a rod having a distal end and a proximal end, and a disposable cleaning head mounted at the distal end of the rod; and one or more cleaning heads unmounted to the cleaning device.

Embodiments of the endotracheal tube cleaning kit can be provided by any of the endotracheal tube cleaning device embodiments described elsewhere herein.

In some embodiments, the kit comprises cleaning heads having various diameters, which can fit tubes of various diameters. In some embodiments of the kit, the rod is configured to be recyclable.

According to an aspect of some embodiments of the present invention there is provided an endotracheal tube cleaning kit, the kit comprises: an endotracheal tube cleaning device comprising one or more rods, and one or more disposable cleaning heads configured to be mounted on one or more of the rods. In some embodiments, the kit comprises a plurality of rods having various lengths, which fit various tube sizes.

Embodiments of the endotracheal tube cleaning kit can be provided by any of the endotracheal tube cleaning device embodiments described elsewhere herein.

According to an aspect of some embodiments of the present invention there is provided an endotracheal tube cleaning system, the system includes an endotracheal tube cleaning device comprising a cleaning head configured to be inserted into an endotracheal tube, and a collector sleeve configured to receive the cleaning head after being removed from the endotracheal tube. According to some embodiments, a collector sleeve is detachably attachable to the endotracheal tube.

According to some embodiments of the invention, the collector sleeve is configured to receive the cleaning device including the cleaning head after being removed from the endotracheal tube. In some embodiments, the collector sleeve is configured to accommodate at least a portion of the cleaning device.

According to some embodiments, the endotracheal tube cleaning device is attachable to the collector sleeve. In some embodiments, the collector sleeve is configured to limit the insertion of the cleaning head through the tube. In some embodiments, the collector sleeve comprises a flexible sleeve and a cap connected at a proximal end of the sleeve. In some embodiments, the cleaning device is attachable to the cap of the collector sleeve.

According to some embodiments of the invention, the collector sleeve is extendable. In some embodiments the collector sleeve is expandable and compressible between a compressed state and an expanded state. In some embodiments, the cleaning device is connected to the extendable collector sleeve and the cleaning head is inserted inside the endotracheal tube when the sleeve assumes a compressed state and the cleaning head is disposed out of the endotracheal tube when the sleeve assumes an expanded state.

In some embodiments of the present invention, in between cleanings, the cleaning device remains at a maximally inserted state in which: at least the rod is disposed within the endotracheal tube with the cleaning head fully extended distally beyond a distal rim of the endotracheal tube. In some embodiments, cleaning of the tube is performed by retracting the cleaning device from the maximally inserted state.

According to some embodiments of the invention, the cleaning head comprises one or more layers having at least a pliable edge. In some embodiments, the proximal layer constitutes the high friction-generating cleaning surface of the cleaning head and the distal layer constitutes the low friction generating layer of the cleaning head. In some embodiments, at least a pliable edge of the cleaning surface is urged against the inner wall of the endotracheal tube when retracting the cleaning device.

In some embodiments, the diameter of the cleaning surface is larger than the diameter of the inner wall of the tube. In some embodiments, the diameter of the cleaning surface is equal or larger than the external diameter of the endotracheal tube (which is equal to the diameter of the outer surface of the tube). In some embodiments, the layers of the cleaning head have different diameters. In some embodiments, the diameter of the low friction-generating surface is larger than the diameter of the high friction-generating cleaning surface. In some embodiments, the diameter of any one of the low friction-generating surface or the high friction-generating surface is between 2 mm and 9 mm. In some embodiments, the diameter of any one of the high friction-generating cleaning surface or the low friction-generating surface is between 4 mm and 8 mm. In some embodiments, the diameter of any one of the surfaces is between 5 mm and 6 mm.

In some embodiments, a retraction contact surface between the high friction-generating cleaning surface and the inner wall of the endotracheal tube during retraction is larger than an insertion contact surface of the high friction-generating cleaning surface and the inner wall of the endotracheal tube during insertion. In some embodiments, the high friction-generating cleaning surface is loosely engaging the inner wall of the endotracheal tube during insertion.

In some embodiments, the retraction contact surface is continuously urged against the inner wall of the endotracheal tube during retraction. In some embodiments, a friction force applied between the high friction-generating cleaning surface and the inner wall of the tube during retraction is larger than a friction force applied between the high friction-generating cleaning surface and the inner wall of the endotracheal tube during insertion. In some embodiments, the friction force applied between the high friction-generating cleaning surface and the inner wall of the tube during retraction is configured to be larger than the friction force between debris accumulated within the endotracheal tube.

According to some embodiments of the invention, the cleaning head comprises a discoid base disposed distally adjacent to the cleaning surface. In some embodiments, the external diameter of the discoid base is smaller than the diameter of the diameter of the cleaning layer. In some embodiments, a peripheral gap is defined between an outer rim of the discoid base and the inner wall of the endotracheal tube.

In some embodiments, the retraction contact surface is formed by deforming the cleaning layer into the gap between the discoid base and the wall of the endotracheal tube. In some embodiments, increasing the contact area of the cleaning layer urged against the inner wall of the tube increases the friction applied by the cleaning layer on the inner wall of the tube. In some embodiments, increasing the friction force by the cleaning layer on the inner wall of the tube increases the amount of debris cleaned by the cleaning device from of the endotracheal tube.

In some embodiments, the elasticity of the discoid base is lower than the elasticity of the cleaning layer. In some embodiments the discoid base is rigid. In some embodiments, the discoid base blocks a deformation of a portion of the cleaning surface over the discoid base. In some embodiments, the cross-section of the undeformed portion of the cleaning layer is equal to the cross-section of the discoid base. In some embodiments, a peripheral gap is defined between an outer rim of the discoid base and the inner wall of the endotracheal tube. In some embodiments, the cleaning layer deforms into the peripheral gap during retraction of the cleaning head.

In some embodiments, the discoid base is round. In some embodiments, the discoid base is shaped as a flat plate. In some embodiments, the gap between the rim of the discoid base and the inner wall of the endotracheal tube is between 0.1 mm and 5 mm. In some embodiments, the gap between the rim of the discoid base and the inner wall of the endotracheal tube is between 0.5 mm and 3 mm. In some embodiments, the gap between the rim of the discoid base and the inner wall of the endotracheal tube is between 1 mm and 2.5 mm. In some embodiments, the discoid base is configured to block instruments or objects inserted within the tube from passing through the cleaning head.

According to some embodiments of the invention, the friction coefficient between the cleaning layer and the inner wall of the endotracheal tube is higher than the friction coefficient of the insertion layer with the inner wall of the endotracheal tube. In some embodiments, during a retraction of the cleaning head, the cleaning layer deforms distally and is urged against the inner wall of the endotracheal tube, thereby cleans the endotracheal tube. In some embodiments, the radius of the insertion layer is larger than the radius of the cleaning layer, by at least the thickness of the cleaning layer.

In some embodiments, during insertion, the insertion layer deforms proximally and interposes the engagement between the cleaning layer and the inner wall of the endotracheal tube, thereby the cleaning head does not clean the tube by whipping debris during insertion. In some embodiments, the ratio between the friction coefficients of the cleaning layer and the insertion layer (with the inner wall of the endotracheal tube) is between 2:1 to 15:1. In some embodiments, the ratio between the friction coefficients of the cleaning layer and the insertion layer (with the inner wall of the endotracheal tube) is between 2:1 to 10:1.

According to some embodiments of the invention, the surface area of the high-friction generating surface is between 2 and 15 times greater than the surface area of the low friction-generating surface. In some embodiments, the surface area of the high-friction generating surface is between 4 and 10 times greater than the surface area of the low friction-generating surface. In some embodiments, the surface area of the high-friction generating surface is between 6 and 8 times greater than the surface area of the low friction-generating surface.

In some embodiments, an insertion limiter is disposed at the proximal end of the rod. In some embodiments, at the maximally inserted state, the insertion limiter engages a proximal end of an endotracheal tube and blocks further insertion of the device into the endotracheal tube.

In some embodiments, at the maximally inserted state, the proximal layer of the cleaning head is facing the distal rim of the tube. In some embodiments, a gap is defined between the proximal layer of the cleaning head and the distal rim of the endotracheal tube. In some embodiments, the gap is in the range of 1 mm to 5 mm. In some embodiments, the gap is in the range of 2 mm to 4 mm. In some embodiments, the gap is in the range of 2.5 mm to 3 mm. In some embodiments, at the maximally inserted state, a gap is defined between the distal end of the cleaning device and the patient tissues. In some embodiments the insertion limiter is adjustable and regulates the gap between the proximal layer and the distal rim of the tube. In some embodiments of the invention, the rod is longer than the endotracheal tube.

In some embodiments, the surfaces of the cleaning head have different thicknesses. In some embodiments the thickness of one or more of the layers is between 0.1 mm and 3 mm. In some embodiments, the thickness of one or more of the layers is between 0.5 mm and 2 mm. In some embodiments, the thickness of one or more of the layers and is between 1 mm and 1.5 mm.

According to some embodiments of the invention, the cleaning head comprises a plurality of ventilation cutouts formed through the proximal layer and the distal layer of the cleaning head. In some embodiments, the ventilation cutouts are radially oriented ending at the peripheral rim of the cleaning head. In some embodiments, a plurality of radial sections is formed in between the cutouts in the cleaning head. In some embodiments, a radial section can be urged into the endotracheal eyelet (Murphy's Eye) at the distal end of the endotracheal tube, so it is cleaned of debris.

According to some embodiments of the invention, the cleaning device comprises a collector sleeve, configured to receive the cleaning head after being removed from the endotracheal tube. In some embodiments, the collector sleeve is configured to receive the cleaning device including the cleaning head after being removed from the endotracheal tube. In some embodiments, the collector sleeve is configured to encompass the cleaning device. In some embodiments, the collector sleeve is configured to limit the insertion of the cleaning head into the tube.

According to some embodiments of the invention, the collector sleeve is extendable. In some embodiments, the collector sleeve is expandable and compressible between a compressed state and an expanded state. In some embodiments, the cleaning device is connected to the extendable collector sleeve and the cleaning head is inserted inside the endotracheal tube when the sleeve assumes a compressed state and the cleaning head is disposed out of the endotracheal tube when the sleeve assumes an expanded state.

According to some embodiments of the invention, the distance between the proximal surface of the cleaning head and the proximal end of the rod is modifiable, prior to insertion, during insertion, or after insertion of the cleaning device within the endotracheal tube. In some embodiments the rod is telescopic.

General

Reference is now made to FIG. 1, which is a side view simplified illustration of an endotracheal tube cleaning device in accordance with some embodiments of the invention. FIG. 1, shows an example of an Endotracheal tube 10, which is inserted inside a patient body P. The endotracheal tube 10 comprises a connector 20 at its proximal end, configured to remain outside a patient body P. The endotracheal tube cleaning device 100 comprises a cleaning head 140, which is configured to be inserted distally into the endotracheal tube 10 via connector 20, and to be retracted proximally out of the endotracheal tube 10. The cleaning device 100 is configured to clean secretions and debris accumulated within the tube 10 when retracting the device 100 out of the endotracheal tube 10. In some embodiments, in between cleaning of the tube 10, the cleaning device 100 remains within the tube 10, while maintaining a continuous air flow communication from/to the lungs throughout the endotracheal tube 10. In some embodiments, the device 100 is configured to be inserted into a clean endotracheal tube 10, without pushing debris inside patient's body (P).

Figure 2:
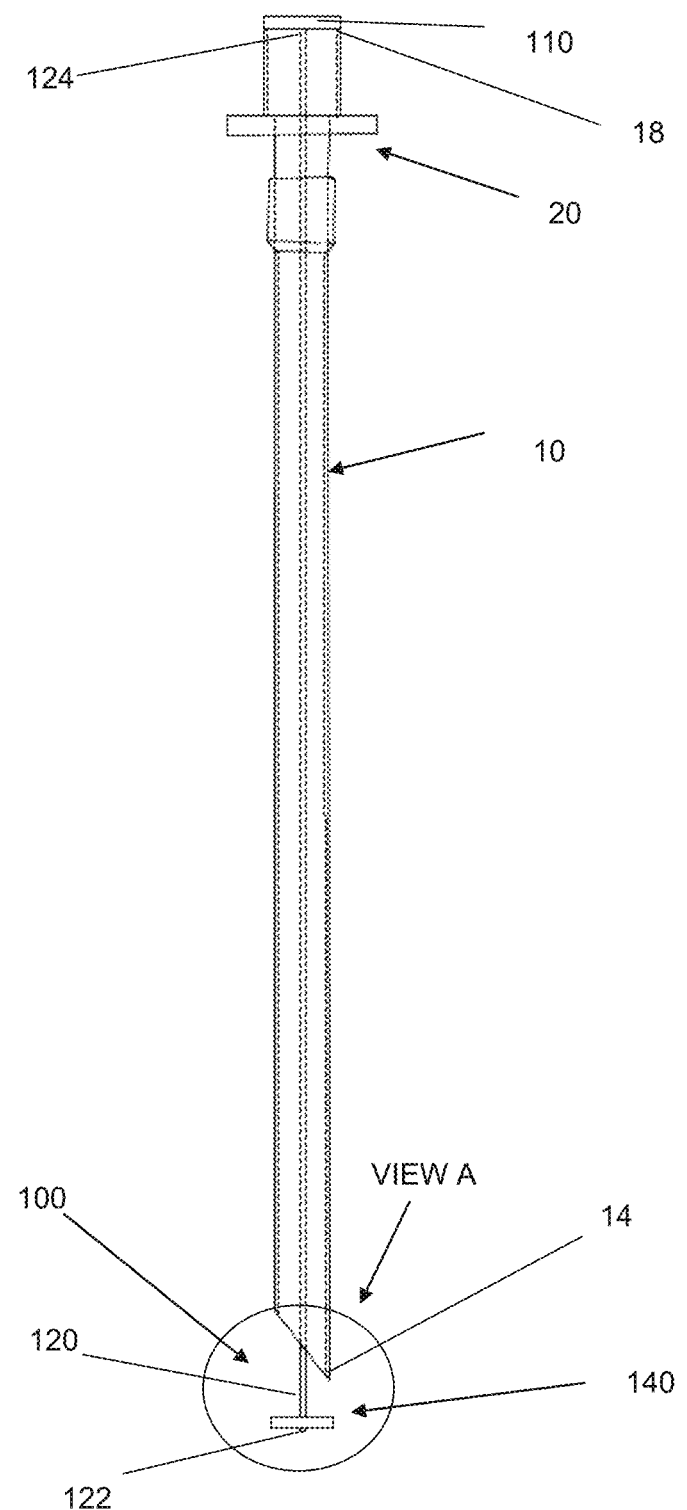
FIG. 2 illustrates a side view simplified illustration of an endotracheal tube cleaning device inserted into an endotracheal tube according to some embodiments of the present invention.

Turning to FIG. 2, which is a side view simplified illustration of an endotracheal tube cleaning device 100 inserted into an endotracheal tube, in accordance with some embodiments of the invention. As shown in FIG. 2, an endotracheal tube cleaning device 100 comprises: a rod 120 having a distal end 122 and a proximal end 124, a cleaning head 140 mounted at the distal end of the rod 122, and an insertion limiter 110. The endotracheal tube 10 comprises a distal tube rim 14 and a proximal tube end 18. In FIG. 2, the endotracheal tube cleaning device 100 is at a maximally inserted state, in which: rod 120 is disposed within the endotracheal tube 10 with the cleaning head 140 fully extended distally beyond the distal rim 14 of the endotracheal tube, and the insertion limiter 110 is configured to engage and the proximal end 18 of the endotracheal tube 10 and block further insertion of the device into tube 10. In some embodiments, cleaning of tube 10 is performed by retracting the cleaning device 100 from the maximally inserted state. In some embodiments, rod 120 is longer than endotracheal tube 10.

Cleaning of the debris according to the embodiments described in the present application is based on applying a high friction force and thereby rub the inner surface of the endotracheal tube. The cleaning head comprises a high friction-generating cleaning surface and low friction-generating surface. The high friction-generating cleaning surface comprises a pliable edge (in some embodiments, the entire cleaning surface is pliable). Movement of the cleaning head within the endotracheal tube in a distal direction (insertion) within the tube flexes the pliable edge proximally so that the low friction-generating surface glides along an inner surface of said endotracheal tube.

Movement of the cleaning head within said endotracheal tube in a proximal direction (retraction) flexes the pliable edge distally bringing the high friction-generating cleaning surface to rub against the inner surface of the endotracheal tube thereby cleaning the inner surface. Some of the aspects of the present invention provide embodiments by which the cleaning head comprises a low friction-generating surface and a high friction-generating surface. The quality of the friction is based on one or a combination of the following structural features of the high and low friction-generating surfaces: texture, contact area, and friction coefficients.

Cleaning Head Types

Reference is now made to FIGS. 3A-3D, which are cross-sectional side view simplified illustrations of an endotracheal tube cleaning device according to some embodiments of the present invention (FIGS. 3A, 3E, 4A, and 6A are not necessarily drawn to proportion). As shown in FIGS. 3A to 3D, cleaning device 100 is configured to clean secretions and debris 90 accumulated within tube 10 when retracting the device 100 out of the endotracheal tube 10.

Figure 3A:
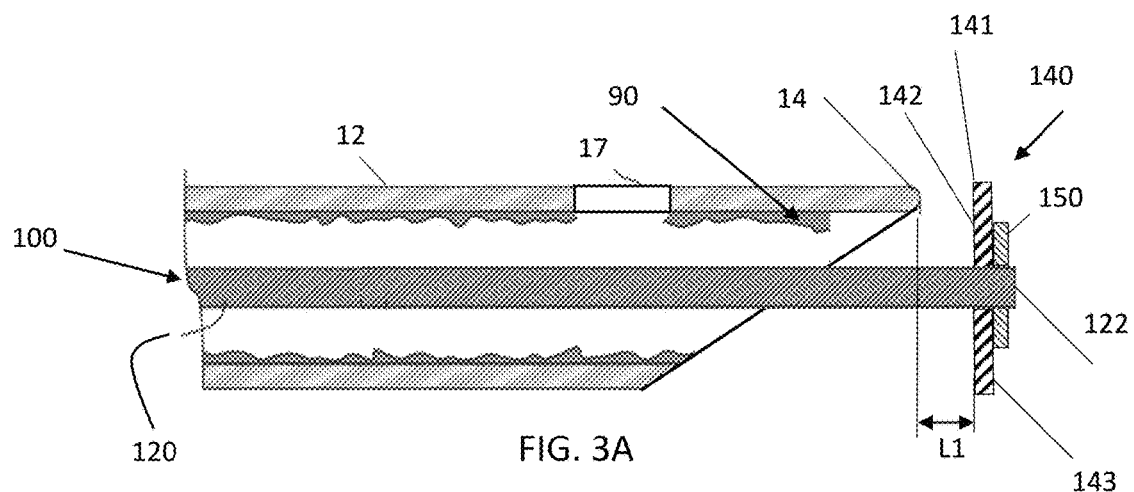
FIGS. 3A, 3B, 3C and 3D are cross section view simplified illustrations of operation of an endotracheal tube cleaning device head inserted into an endotracheal tube according to some embodiments of the present invention.

In FIG. 3A, the cleaning head 140 comprises a cleaning layer 141 comprising a proximal high friction-generating cleaning surface 142. The cleaning device 100 is at a maximally inserted state, in which the cleaning layer 141 is disposed beyond rim 14 of tube 10, and a gap L1 is defined between the cleaning surface 142 and the distal rim 14 of the tube. A continuous airflow within endotracheal tube 10 is maintained by having gap L1 while the cleaning device 100 is inserted within tube 10. Thereby, the cleaning device 100 is stowed at a maximally inserted state between cleanings. In some embodiments, devices can be inserted through the endotracheal tube 10 and the gap L1 for the treatment of a patient while the cleaning device 100 is disposed within the endotracheal tube 10. Thereby, the cleaning device 100 can be stowed within the endotracheal tube 10 with a minimal disturbance to the patient and to the medical personnel until a cleaning of the endotracheal tube is required. In some embodiments, the cleaning device is configured to be stowed in the endotracheal tube in between cleanings, in a maximally inserted state in which at least the rod is disposed within the endotracheal tube, the cleaning head is fully extended distally beyond a distal rim of the endotracheal tube, and the insertion limiter engages a proximal rim of the endotracheal tube and blocks further insertion of the device into the tube.

In some embodiments, at the fully extended state, the head is configured to be disposed in a lumen of the pulmonary bronchi between the bronchi carina and the distal rim of the endotracheal tube.

In some embodiments, the gap L1 is in the range of 1 mm to 5 mm. In some embodiments, L1 is in the range of 2 mm to 4 mm. In some embodiments, L1 is in the range of 2.5 mm to 3 mm.

As shown in FIG. 3A, the diameter of the cleaning layer 141 is larger than the diameter of the inner wall 13 of the tube. During insertion into the endotracheal tube 10, at least the flexible edge of the cleaning surface 142 is deformed proximally when the cleaning layer 141 is articulated over the proximal rim 18 (seen in FIG. 2) of the endotracheal tube 10. During retraction into the endotracheal tube 10 from being stowed at a maximally insert state, at least the flexible edge of the cleaning surface 141 is deformed distally when the cleaning layer 141 is articulated over the distal rim 14 of the endotracheal tube 10. In some embodiments, the diameter of the cleaning layer 141 is at least about the diameter of the external tube wall 12. In some embodiments the diameter of the cleaning layer 141 is between 2 mm to 9 mm. In some embodiments the diameter of the cleaning layer 141 is between 4 mm and 8 mm. In some embodiments the diameter of the cleaning layer 141 is between 5 mm and 6 mm.

Figure 3B:
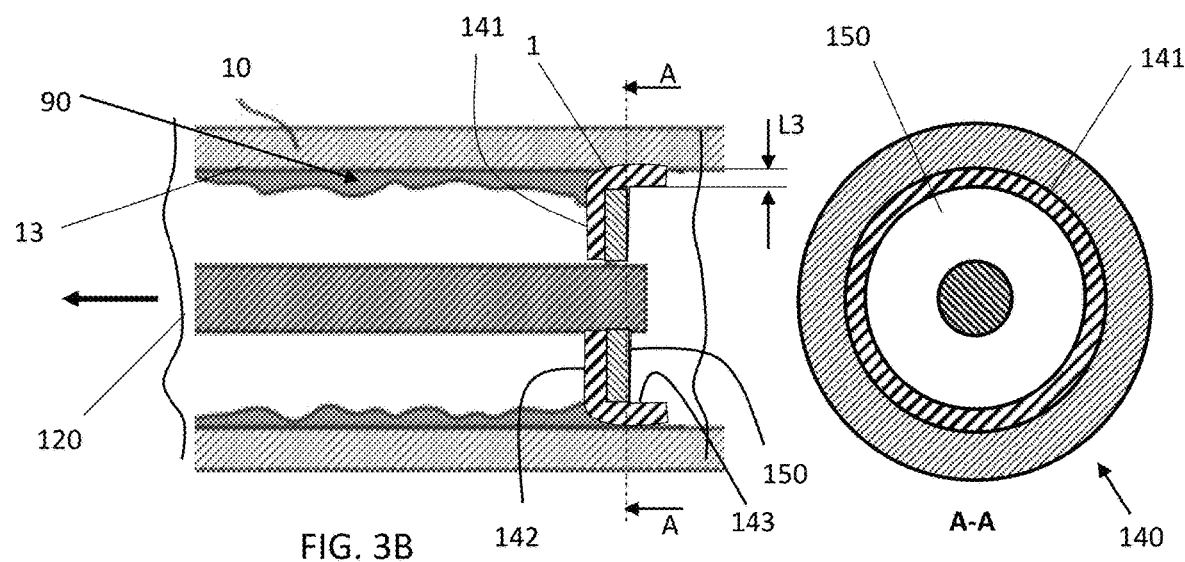

In some embodiments of the invention, the cleaning layer 141 comprises a proximal high friction-generating cleaning surface 142, which is formed on or extending from a low friction-generating cleaning surface. FIGS. 3A to 3D, illustrated an embodiment of the present invention in which the cleaning head 140 comprising a distal discoid base 150 disposed adjacent to the cleaning layer 141. As shown in FIG. 3B, the discoid base 150 is rigid and partially limits a distal deformation of the cleaning layer 141 cross-section over the discoid base 150 during a retraction of the cleaning head 140. In some embodiments, the cleaning head 140 comprises the discoid base and the cleaning body is merely a pliable edge mounted to a proximal portion of the edge of the discoid base.

A peripheral gap L3 is defined between the external rim of the discoid base 150 and the inside surface 13 of the endotracheal tube 10. As shown in section A-A, the cleaning layer 141 deforms into the peripheral gap L3 during retraction of the cleaning head 140, so that the cleaning layer 141 is urged against the inner wall 13 of the endotracheal tube 10 by the external rim of the discoid base 150. A retraction contact surface 1 is defined between the cleaning surface layer 142 and the inner wall 13 of the tube 10 when having a cleaning layer 141 deformed into the peripheral gap L3 and pressed against the inner wall 13 of the tube 10.

Figure 3C:
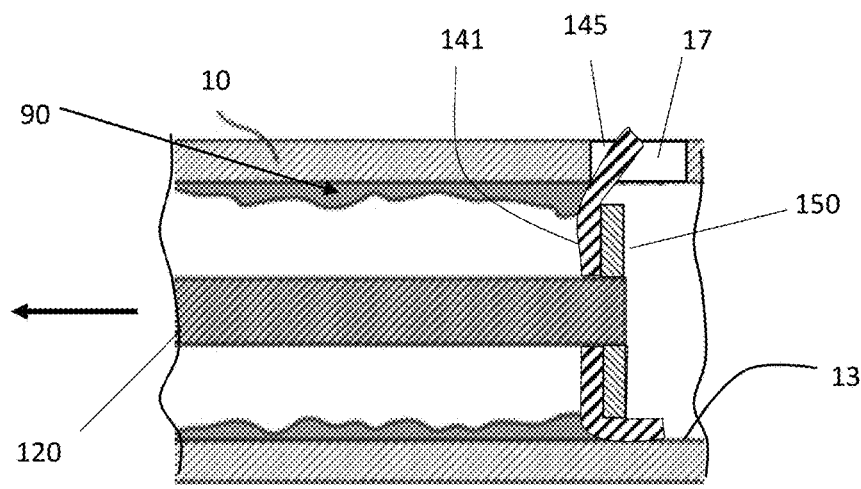

As shown in FIG. 3C, when the cleaning head 140 is retracted, a section 145 of the resilient cleaning layer 141 bends into the "murphy's eye" configuration 17 (standard to ET tubes) formed in proximity to the distal rim 14 of an endotracheal tube 10, so section 145 rubs and cleans debris accumulated within the "murphy's eye".

Figure 3D:
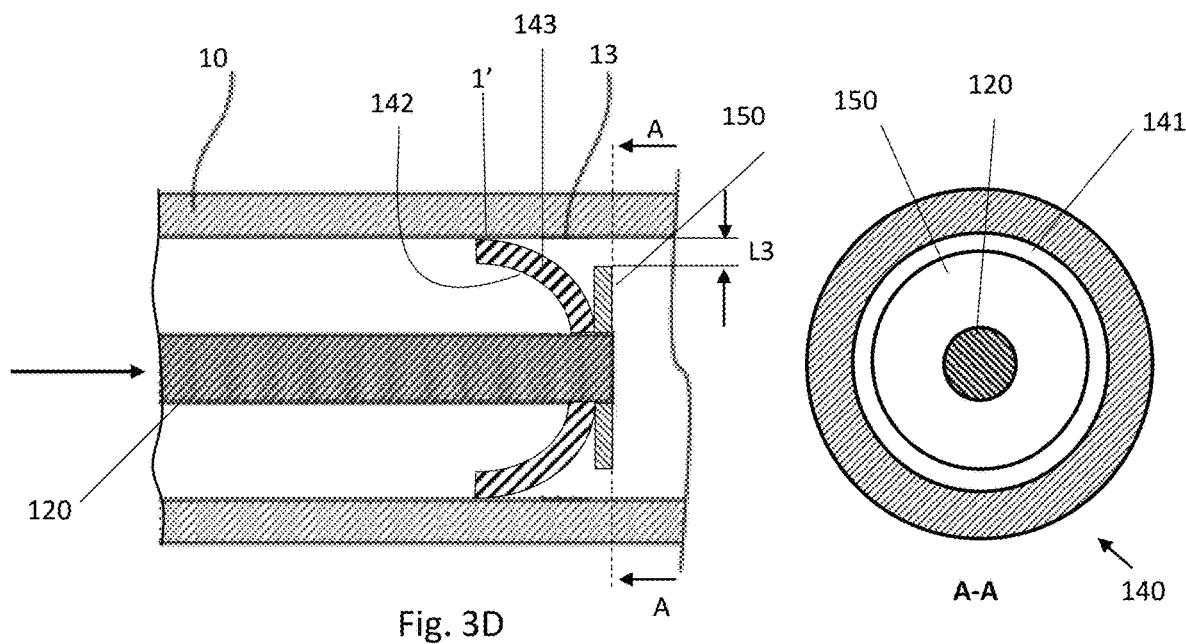

As shown in FIG. 3D, when inserting the cleaning device 100 into the tube 10, the cleaning layer 141 deforms proximally. During insertion, the gap L3 between the external rim of the discoid base 150 and the inner wall 13 of the endotracheal tube 10 is maintained between the external rim of the discoid base 150 and the inner wall 13 of the endotracheal tube 10, free of a cleaning layer 141. The gap can increase or decrease during insertion due to axial and angular movements of the cleaning head within the tube.

As shown in FIG. 3D, an insertion contact surface 1' is defined between the proximal surface layer 143 of the cleaning layer 141 and the inner wall 13 of the tube 10 during insertion. During insertion, the flexible edge of the cleaning surface 142 deforms proximally away of the gap L3 between the external rim of the discoid base 150 and the inner wall 13 of the endotracheal tube 10. Thereby, the cleaning surface 142 is not urged inside the gap L3 and is not urged by the discoid base 150 against the wall 13 of the tube. As a result, the area of the insertion contact surface 1' is smaller than the area of the retraction contact surface 1 and the friction of the high friction contact surface 1 on the inner wall 13 of the tube is higher than the friction applied by the insertion contact surface 1' on the inner wall of the tube. Thereby, during retraction, the retraction contact surface rubs debris 90 from the inner wall 13 of the endotracheal tube 10 by a higher cleaning force, and during insertion, the insertion contact surface glides along the inner wall 13 of the endotracheal tube 10. In some embodiments as seen in FIG. 3D, the cleaning surface 142 is not in contact with the wall 13 of the tube during insertion. In some embodiments as seen in FIG. 3D, the majority of the proximal surface layer 143 of the cleaning layer 141 does not engage the inner wall 13 of the tube 10 during insertion.

In some embodiments, the high friction-generating surface 142 and the low friction-generating surface 143 comprise different textures. In some embodiments, the high friction-generating surface 142 and the low friction-generating surface 143 differ in their roughness. In some embodiments the high friction-generating surface 142 and the low friction-generating surface 143 are made of different materials, for example, materials having different friction coefficients. At least some of these embodiments further control the force applied by at least one of the high friction-generating surface 142 and the low friction-generating surface 143 on the inside surface 13 of the tube 10.

In some embodiments, the gap L3 between the external rim of the discoid base 150 and the inner wall 13 of the endotracheal tube 10 is between 0.1 mm and 5 mm. In some embodiments, the gap L3 between the external rim of the discoid base 150 and the inner inner wall 13 of the endotracheal tube 10 is between 0.5 mm and 3 mm. In some embodiments, the gap L3 is between 1 mm and 2.5 mm. In some embodiments discoid base 150 is configured to block instruments or objects inserted within the endotracheal tube 10 from passing through the cleaning head 140. As shown in FIGS. 3A to 3E, discoid base 150 is round and is shaped as a flat plate. In some embodiments, the discoid base is non-circular and/or having a longitudinal geometry other than a flat plate (e.g. cylindrical, cylindrical with a flange). In some embodiments, the discoid base is a resilient layer.

Figure 3E:
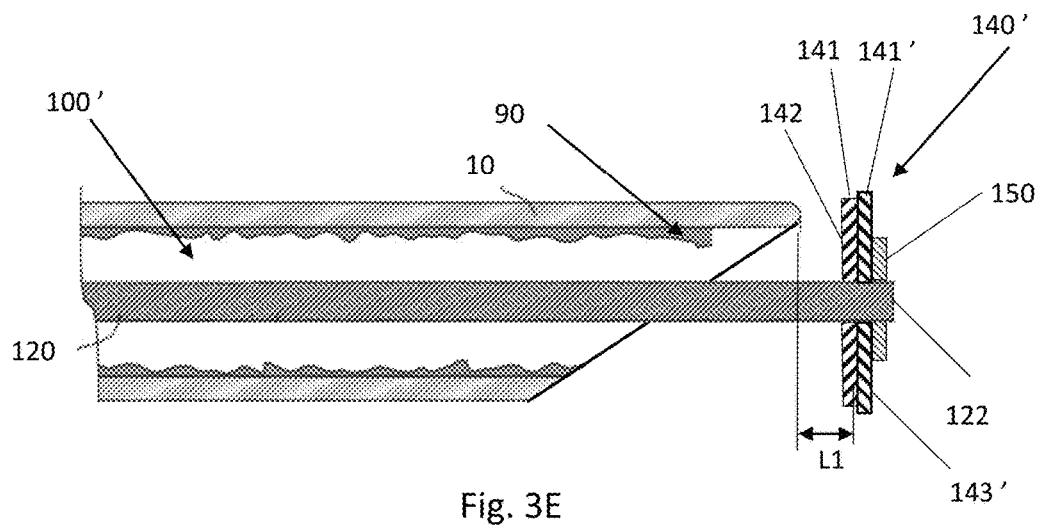
FIG. 3E is a side view simplified illustration of an endotracheal tube cleaning device multi-layered head according to some embodiments of the present invention.

As shown in FIG. 3E, in some embodiments, cleaning layer 141 comprises more than one layer. In some embodiments layers 141/141' are made of different materials, for example, materials having different friction coefficients. In some embodiments, the layer 141' is made of Teflon. In some embodiments, the layers comprise different textures. In some embodiments, the distal surface 143' of layer 141' and the proximal cleaning surface 142 of layer 141 differ in their roughness. In some embodiments, the layers 141/141' differ in their thicknesses and/or geometries.

According to embodiments shown in FIG. 3E, both layers enter the gap between the discoid base 150 and the tube wall 13 during retraction, which resembles the embodiments shown in FIG. 3B. During insertion, (as described hereinafter in FIG. 4C) the layer 141' interpose at least partially an engagement between the cleaning layer 141 and the inner wall 13 of the endotracheal tube 10. Thereby, the embodiment of FIG. 3E resembles both the retraction mechanism, described in FIG. 3B and the insertion mechanism, described hereinafter in FIG. 4C.

Figure 4A:
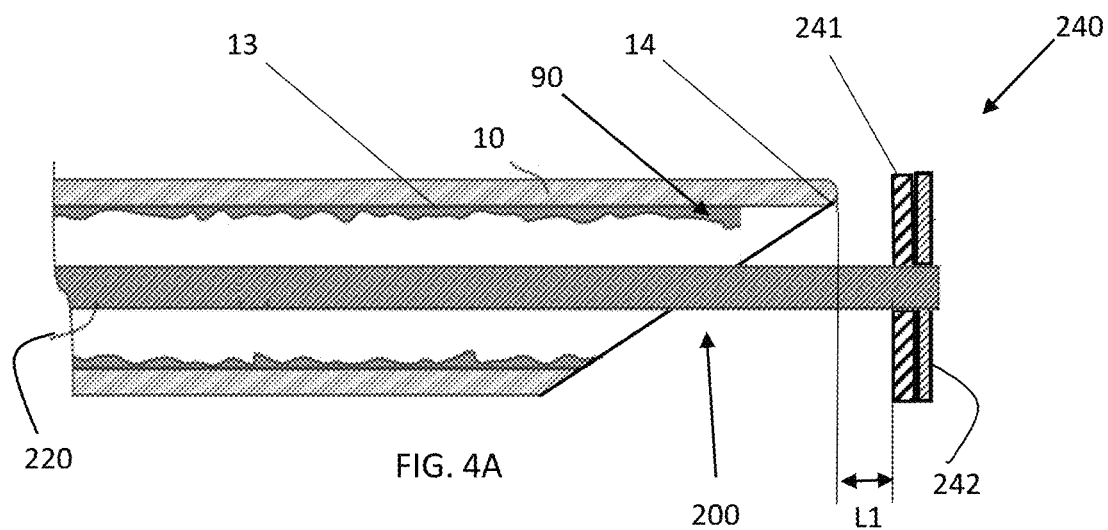
FIGS. 4A, 4B and 4C are cross section view simplified illustrations of an operation of an endotracheal tube cleaning device head inserted into an endotracheal tube according to some embodiments of the present invention.
Figure 4B:
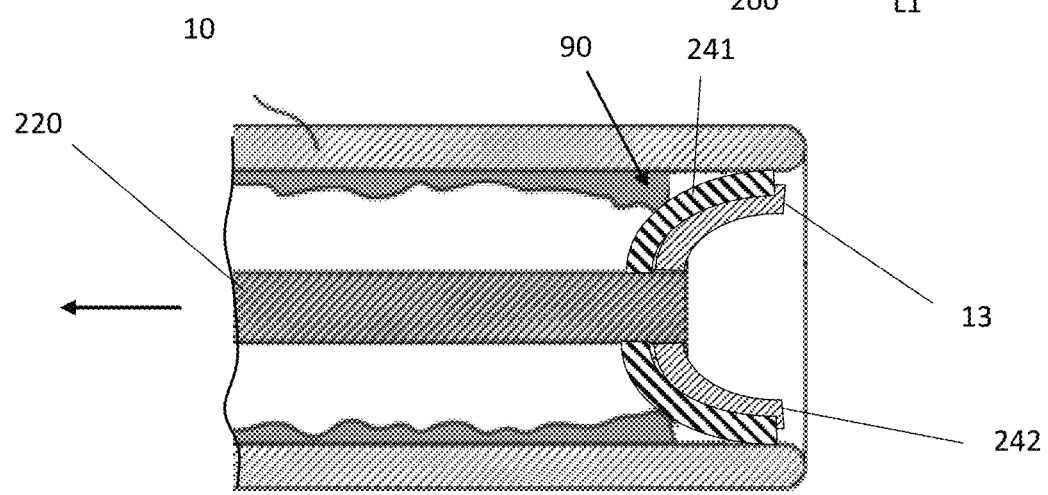
Figure 4C:
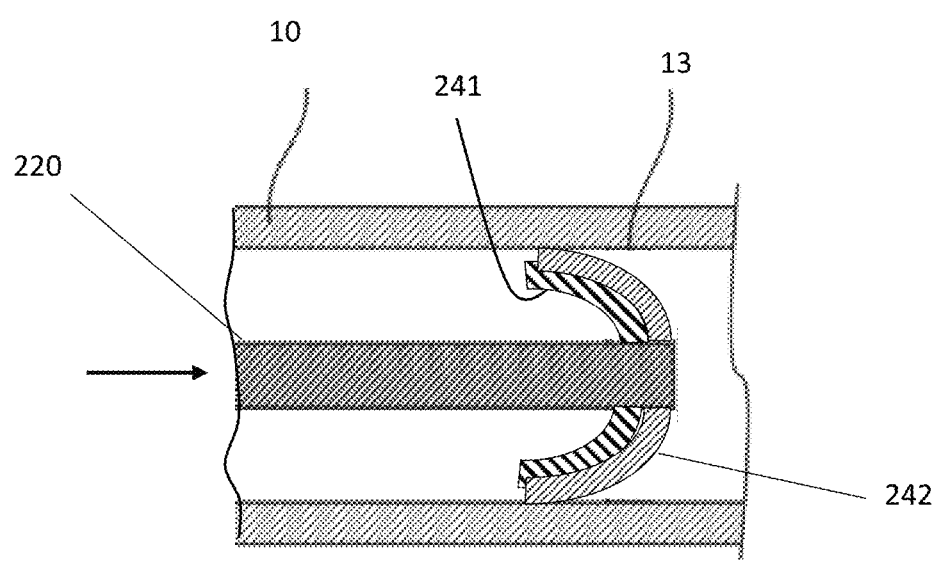

Reference is now made to FIGS. 4A to 4C, which are cross sectional side view simplified illustrations of an endotracheal tube cleaning device inserted into an endotracheal tube according to some embodiments of the present invention. The cleaning device 200 is configured to clean secretions and debris accumulated within the tube 10 when retracting the device 200 out of the endotracheal tube 10. The cleaning device 200 differs of cleaning device 100 described in FIGS. 3A to 3D in the structure and the operation of the cleaning head 240 compared to cleaning head 140.

For example, both cleaning devices 100 and 200 are configured to be inserted to a maximally inserted state, in which a gap L1 is formed between the proximal cleaning layer 141/241 of the cleaning head and the distal rim 14 of the tube. The layers 241/242 are larger than the diameter of the inner wall 13 of the tube. Thereby deform proximally during insertion and deform distally during retraction. Thereby, the description hereinafter focuses on the difference characterized by the cleaning head 240 embodiment.

As shown in the exemplary embodiment depicted in FIGS. 4A to 4C, the cleaning head 240 comprises two layers, a distal low friction-generating insertion layer 242 and a proximal high friction-generating cleaning layer 241. The cleaning head 240 is configured to have the cleaning layer 241 urged at least partially against the inside tube wall 13 when retracting the cleaning head 240 out of the endotracheal tube.

In some embodiments, the layers 241/242 are made of different materials, for example, materials having different friction coefficients. In some embodiments, the friction coefficient between the cleaning layer 241 and the inner wall 13 of the endotracheal tube 10 is higher than the friction coefficient between the insertion layer 242 and the inner wall 13 of the endotracheal tube 10. Thereby, the insertion of the cleaning head 240 requires a lower force than its retraction within the endotracheal tube 10. In some embodiments the ratio between the friction coefficients of the cleaning layer 241 and the insertion layer 242 with the inner wall 13 of the endotracheal tube 10 is at least 2:1.

In some embodiments, the insertion layer 242 is made of a Teflon. In some embodiments, the cleaning layer 241 is made of a sponge-like material. In some embodiments, the layers 241/242 comprise different textures. In some embodiments, the distal surface of layer 242 and the proximal cleaning surface of layer 241 differ in their roughness. In some embodiments, the layers 241/242 different in their thicknesses and/or geometries.

As shown in FIG. 4B, when withdrawing the cleaning device 200 proximally (in a direction opposite to the distal rim 14 of the endotracheal tube 10), the layers 241 and 242 deform distally so that the cleaning surface 241 is urged against the inner wall 13 of the endotracheal tube 10. As shown in FIG. 4C, when inserting the cleaning device 200 into the tube 10 distally (in a direction towards the distal tube rim 14), the insertion layer 242 deforms proximally and interpose at least partially an engagement between the cleaning layer 241 and the inner wall 13 of the endotracheal tube 10.

The characteristic of layers 241/242 is selected so that the friction between layer 241 and the inner wall 13 of the tube is high than the friction between wall 13 and layer 242. Thereby, during retraction, the cleaning surface 241 has high friction the inner wall 13 of the endotracheal tube 10 that is sufficient to rubs debris 90 from the inner wall 13 of the endotracheal tube 10. However, during insertion the friction decreases due to interposing between the high friction generating surface on layer 241 and wall 13 so that the layer 242 glides along the inner wall 13 of the endotracheal tube 10 with low friction which does not remove debris, therefore does not push debris (into patient body) during insertion.

In some embodiments, the cleaning layer 241 and the insertion layers 242 have different thicknesses. In some embodiments the thickness of any one of the cleaning layer 241 and the insertion layer 242 is between 0.1 mm and 3 mm. In some embodiments the thickness of each of the layers 241 and 242 is between 0.5 mm and 2 mm. In some embodiments the thickness of each of the layers 241 and 242 is between 1 mm and 1.5 mm.

Figure 5A:
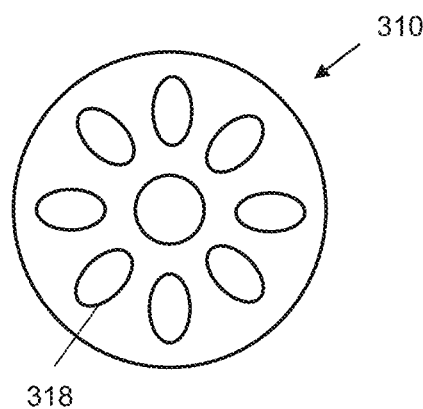
FIGS. 5A, 5B, 5C and 5D are top and side view simplified illustrations of an endotracheal tube cleaning device heads according to some embodiments of the present invention.
Figure 5B:
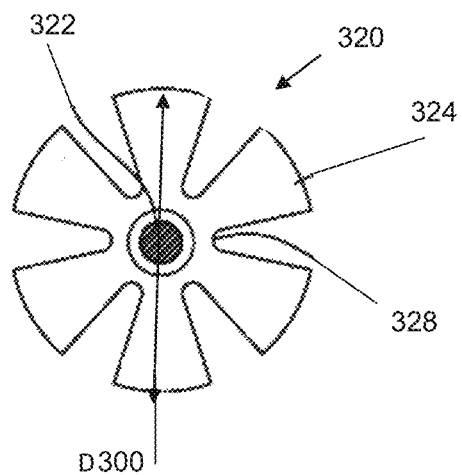
Figure 5C:
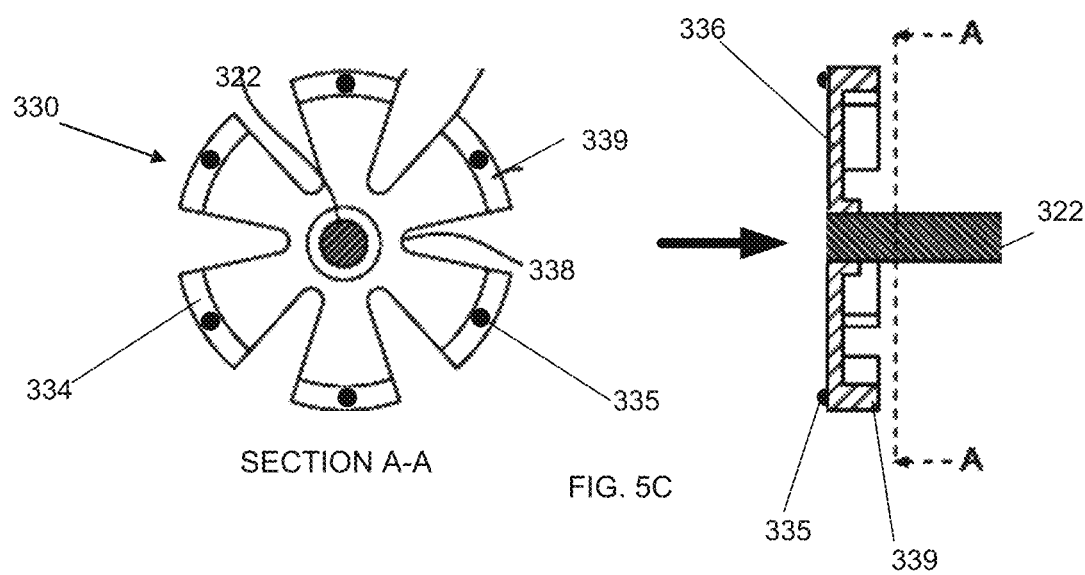
Figure 5D:
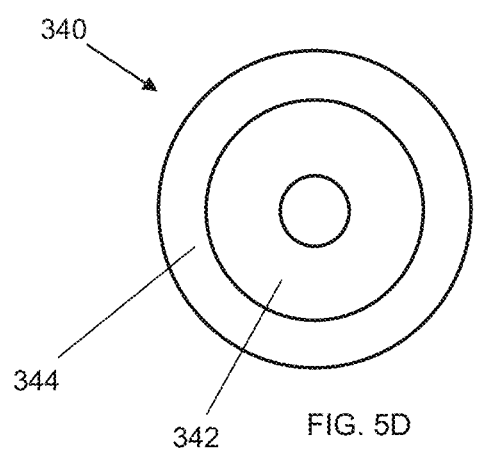

Turning to FIGS. 5A to 5D, which are side view simplified illustrations of an endotracheal tube cleaning device according to some embodiments of the invention. As shown in FIGS. 5A, 5B and 5C, according to some embodiments of the invention, the cleaning heads comprise one or more cleaning layers 310/320/330 that comprise a plurality of cutouts 318/328/338. In some embodiments, the cutouts 328/338 are radial ending at the peripheral edge of the cleaning head 320/330. In some embodiments, the cutouts 318/328/338 enable ventilation (air passage within the endotracheal tube 10). In some embodiments, a plurality of radial sections 324/334 is formed in between cutouts 328/338 in the cleaning head 320/330. In some embodiments, radial sections 324/334 are urged into a "murphy's eye" configuration (similar to the example depicted in FIG. 3C) formed in proximity to the distal rim 14 of an endotracheal tube 10, so it is cleaned of debris accumulated at the "murphy's eye".

In some embodiments, as shown in FIG. 5C, the cleaning head layer 330 comprises one or more surfaces protruding transversely to a base layer 336, distal protrusions 335 and/or proximal protrusions 339. In some embodiments, the cleaning layer has a uniform thickness. In some embodiments, the cleaning layer has a varying thickness.

As shown in the explementary embodiment 5D, the cleaning layer 340 of a cleaning head comprises sections 342 and 344 formed of one or more materials. In some embodiments, the sections differ in their friction coefficients. For example, the friction coefficient between section 344 and the inner wall 13 of the endotracheal tube 10 is higher with than the friction coefficient between section 342 and the inner wall 13 of the endotracheal tube 10. In some embodiments sections 342 and 344 have varying thickness. In some embodiments the thickness of section 344 is higher than the thickness of section 342.

Figure 6A:
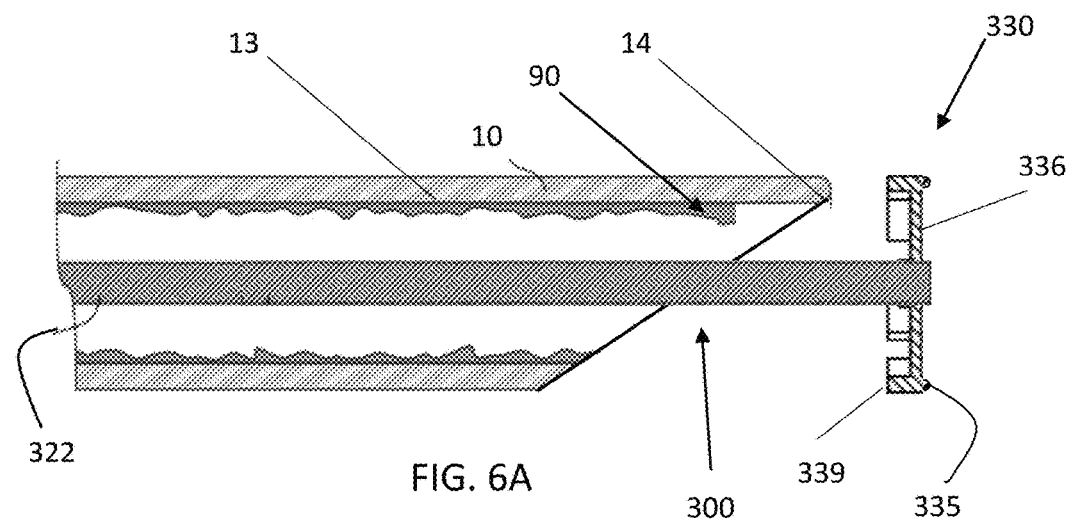
FIGS. 6A, 6B and 6C are cross section simplified illustrations of operation of an endotracheal tube cleaning device head inserted into an endotracheal tube according to some embodiments of the present invention.
Figure 6B:
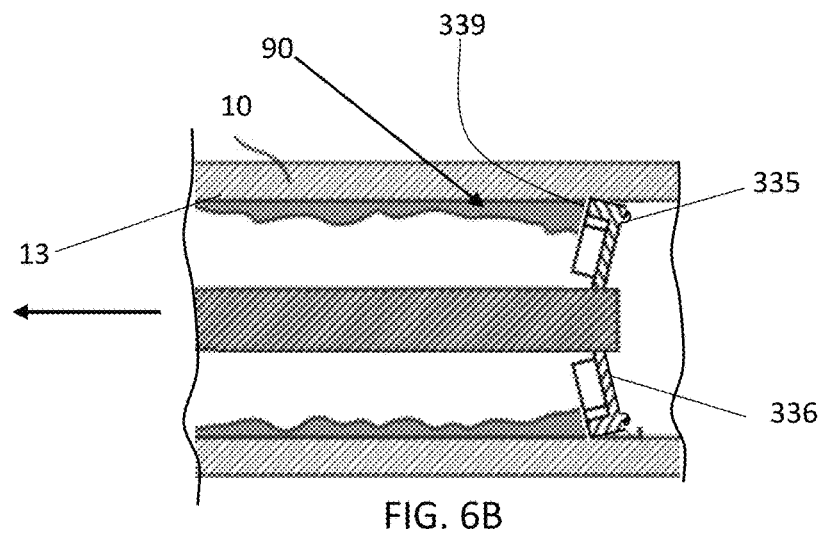
Figure 6C:
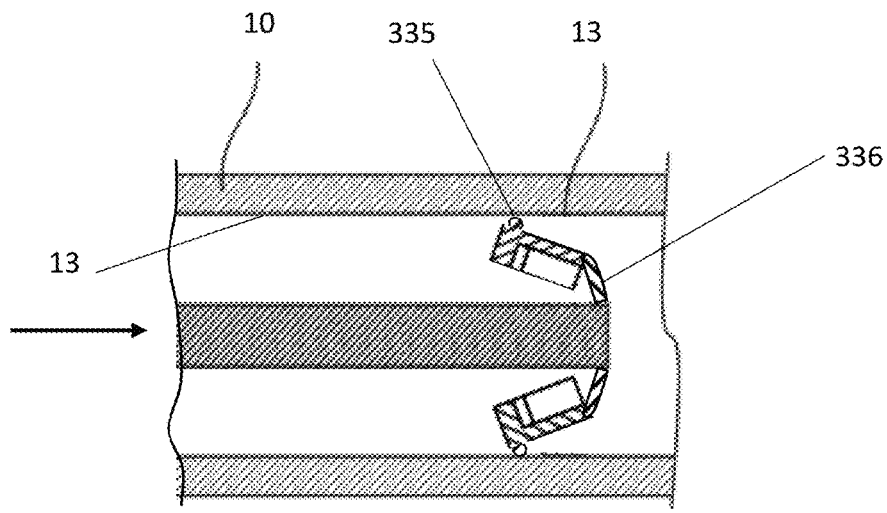

Reference is now made to FIGS. 6A to 6C, which are cross sectional side view simplified illustrations of an endotracheal tube cleaning device inserted into an endotracheal tube according to some embodiments of the present invention. The cleaning device 300 is configured to clean secretions and debris accumulated within the tube 10 when retracting the device 300 out of the endotracheal tube 10. The cleaning device 300 differs of cleaning devices 100/200 described in FIGS. 3A to 4C in the structure and the operation of the cleaning head 330 compared to cleaning heads 140/240. For example, the cleaning devices 100, 200 and 300 are configured to be inserted to a maximally inserted state, to maintain a gap between the proximal surface of the cleaning layer 141/241/339 of the cleaning head 140/240/330 and the distal rim 14 of the tube. The cleaning layers 141/241/339 are larger than the diameter of the inner wall 13 of the tube. Thereby deform proximally during insertion and deform distally during retraction. Thereby, the description hereinafter for FIGS. 6A to 6C focuses on the cleaning head 330 embodiment.

As shown in the exemplary embodiment depicted in FIGS. 6A to 6C, the cleaning head 330 comprises one or more surfaces protruding transversely to a base layer 336: distal protrusions 335 and/or proximal protrusions 339. As shown in FIG. 6B, the proximal protrusions 339 are formed at the cleaning layer 330 to increase the contact area between the cleaning layer 300 and the inner wall 13 of the endotracheal tube 10 during retraction. As shown in FIG. 6C, the distal protrusions 335 are formed at the cleaning layer 330 to limit the contact area between the cleaning layer and the inner wall of the endotracheal tube during insertion of the cleaning device 300 into the endotracheal tube 10 towards the distal rim 14 of the endotracheal tube.

The cleaning head 330 is configured to urge the cleaning surface 339 at least partially against the inside tube wall 13 when retracting the cleaning head 330 out of the endotracheal tube. The diameter of the cleaning head 330 is larger than the diameter of the inner tube wall 13, thus the cleaning surface 339 is in contact with the endotracheal tube wall 13 at least when being retracted. In some embodiments, the diameter of the cleaning head 330 is at least about the diameter of the external tube wall 12. In some embodiments the diameter of the cleaning head 330 is between 2 mm to 9 mm. In some embodiments, the diameter of the cleaning head 330 is between 4 mm and 8 mm. In some embodiments, the diameter of the cleaning head 330 is between 5 mm and 6 mm.

As shown in FIG. 6B, when retracting the cleaning device 300 in a direction opposite to the distal rim 14 of the endotracheal tube 10, the cleaning head 330 deforms distally so that the cleaning surface 339 is urged against the inner wall 13 of the endotracheal tube 10 and cleans debris 90 accumulated along the inner tube wall 13.

As shown in FIG. 6C, when inserting the cleaning device 300 into the tube 10 in a direction towards the distal tube rim 14, the cleaning head 330 deforms proximally and expose the protrusions 335 to engage the inner wall of the endotracheal tube 10.

In some embodiments, the distal protrusions 335 and the proximal protrusions 339 are made of different materials. In some embodiments, the friction coefficient between the proximal protrusions 339 and the inner wall 13 of the endotracheal tube 10 is higher than the friction coefficient between the protrusions 335 and the inner wall 13 of the endotracheal tube 10.

Figure 7A:
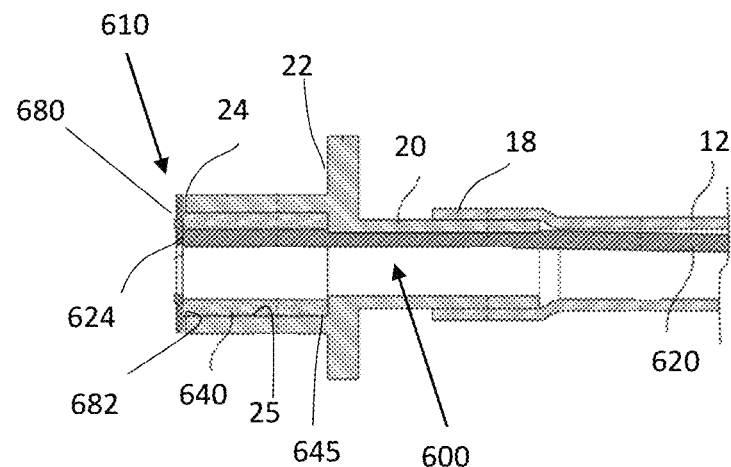
FIGS. 7A, and 7B are cross section view simplified illustrations of insertion limiters for an endotracheal tube cleaning device inserted into an endotracheal tube according to some embodiments of the present invention.
Figure 7B:
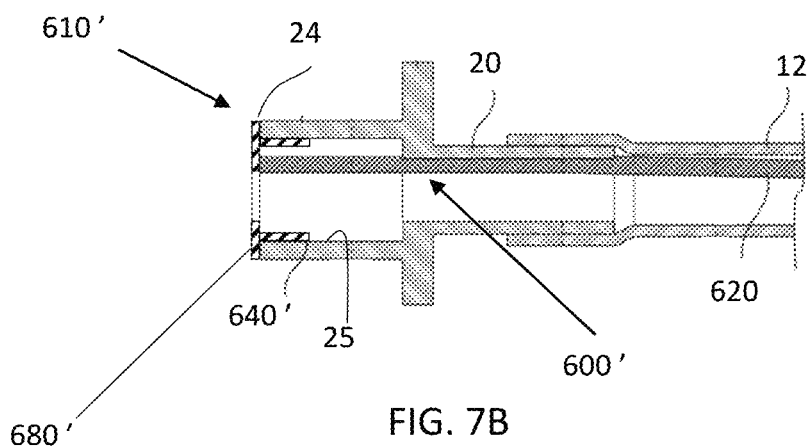

According to some embodiments, at the maximally inserted state, the insertion of the cleaning device into the endotracheal tube is restricted, with the aim of for example, to avoid damaging the Carina or other internal organs. Turning to FIGS. 7A and 7B, which illustrate cross sectional side view simplified illustrations of an endotracheal tube cleaning device 600/600' according to some embodiments of the present invention. As shown in FIGS. 7A and 7B, the cleaning device 600/600' comprises an insertion limiter 610/610' configured to diametrically engage a connector end 24 (or an outer tube end 18 if the tube is absent a connector 20). The insertion limiter 610/610' comprises a cap 680 having a fitting extension 640/640' protruding distally from a distal face 682 of the cap 680. The cleaning devices 600/600' comprises a cleaning head (not shown) which can be any of the cleaning head embodiments described elsewhere herein.

The proximal end 624 of the rod 620 is attachable to cap 680, thereby, the rod 620 and the insertion limiter 610 longitudinally move longitudinally together. In the exemplified embodiment shown in FIG. 7A, cap 680 is configured to engage the distal end 24 of connector 20, thereby limiting the insertion of the rod 620 into the tube 10 upon an engagement of face 682 with distal end 24. In the exemplified embodiment shown in FIGS. 7A/7B, the tube fitting extension 640 is configured to engage the inside surface 25 of connector 20. In some embodiments, as shown in FIG. 7A, the fitting extension 640 is configured to engage connector face 22, thereby limiting of the insertion of the rod 620 into the tube 10. In some embodiments, as shown in FIG. 7B, the fitting extension 640' is short so that the insertion is blocked by the engagement of surface 680' with the distal rim 24 of the connector 20. In some embodiments (not shown) a limiter is adjustably connected to the rod 620, wherein the insertion limiter 610 is configured to adjust gap L1.

According to some embodiments of the invention, the distance between the cleaning head and the outer end of the rod is modifiable, prior or after insertion within the endotracheal tube. In some embodiments, the rod is telescopic.

Biofilm Collector

Figures 8A, 8B, 8C:
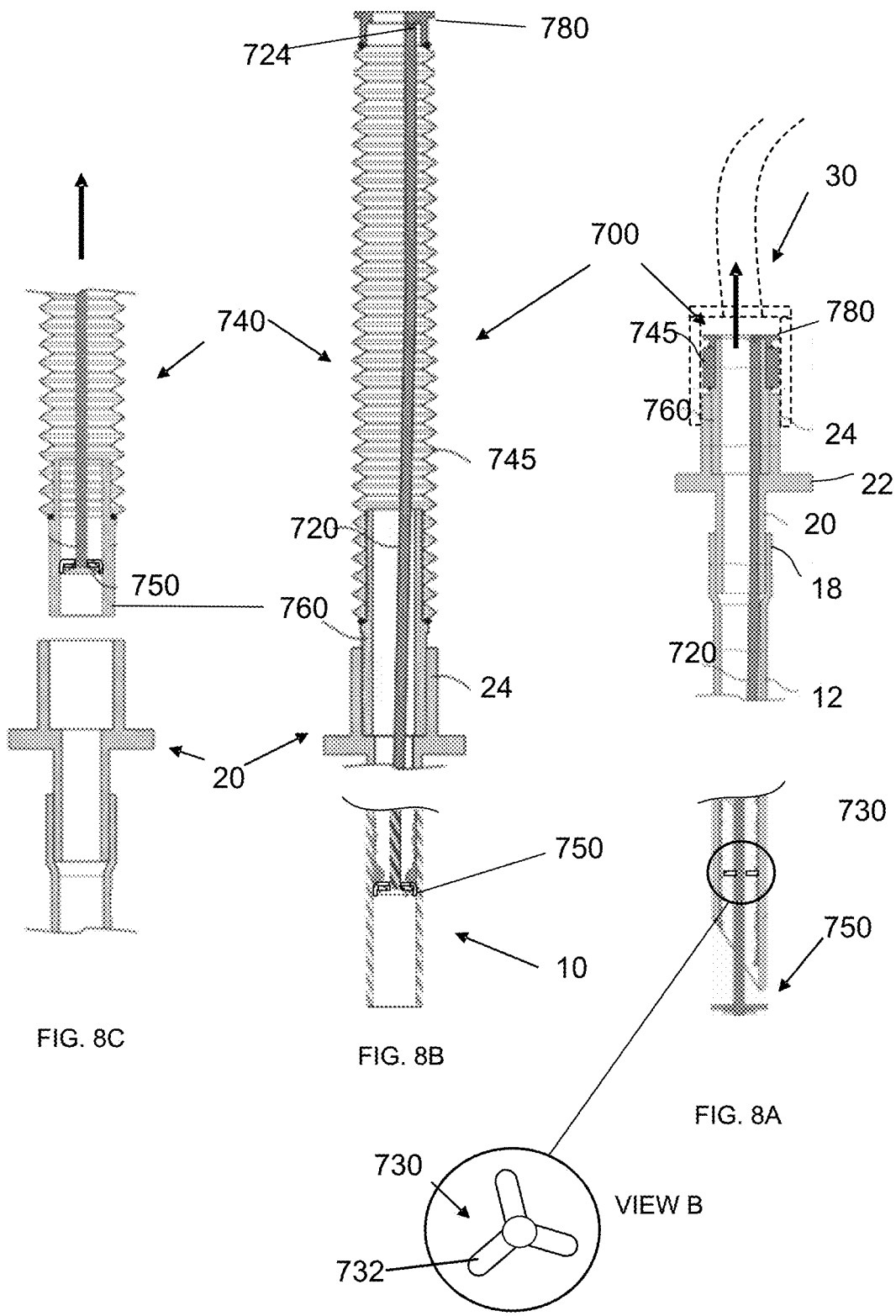
FIGS. 8A, 8B and 8C are cross section view simplified illustrations of an endotracheal tube cleaning device collector sleeve according to some embodiments of the present invention.

Reference is now made to FIGS. 8A to 8C, which illustrate cross sectional side view simplified illustrations of an endotracheal tube cleaning system 700 according to some embodiments of the present invention. As shown in FIGS. 8A to 8C, the system 700 comprises an endotracheal tube cleaning device 720 comprising a cleaning head 750 configured to be inserted into an endotracheal tube 10, and a biofilm collector sleeve 740, configured to receive secretions, mucus and/or debris removed by cleaning head 750 during withdrawal of the device from the endotracheal tube 10. In some embodiments, the collector sleeve 740 comprises at its distal end a sleeve connector 760, which is detachably attachable to endotracheal tube 10 or to an endotracheal tube connector 20.

A potential advantage of having an endotracheal tube cleaning system having a biofilm collector sleeve receiving the cleaning head after being removed from the endotracheal tube is in that a biofilm collector:
(a) enables a fast and clean disposal of the endotracheal tube cleaning device after being removed from the endotracheal tube,
(b) encloses the endotracheal tube cleaning device within a collector sleeve enables keeping the surrounding environment clean and
(c) allows a simple and quick replacement of a used cleaning device with a new one prior to an accumulation of debris on the endotracheal tube.

As shown in FIG. 8C, in some embodiments, the volume of the collector sleeve 740 is configured to receive and encompass the cleaning device 720 including the cleaning head 750 after being removed from the endotracheal tube 10.

As shown in FIGS. 8A to 8C, the collector sleeve 740 comprises a flexible sleeve 745 and a cap 780 connected at a proximal end of the sleeve. In some embodiments, sleeve 745 is stretchable. In some embodiments as shown in FIGS. 8A to 8C, sleeve 450 is shaped as a flexible accordion, having a fully compressed state (FIG. 8A), an expanded state (FIG. 8B), expanded state (FIG. 8C). In some embodiments, the cleaning device 720 is connected to cap 780, which can be used to longitudinally move the cleaning device 720 within the tube 10. The cleaning head 750 is inserted inside the endotracheal tube 10 when the sleeve assumes a compressed state (FIG. 8A) and the cleaning head 750 is disposed out of the endotracheal tube 10 when the sleeve assumes a fully expanded state (FIG. 8C). In some embodiments, once the cleaning head 750 is disposed and encompassed within the sleeve 745, the endotracheal tube cleaning system 700 can be detached from the endotracheal tube 10, while keeping it protected and untouched by the endotracheal personnel servicing the patient and a new endotracheal tube cleaning system 700 can be attached to the endotracheal tube. In some embodiments, the endotracheal tube cleaning system 700 is detachable from the endotracheal tube 10 in any state of the sleeve. The replacement procedure of the cleaning device 720 may require detaching devices connected to the endotracheal tube 10 cleaning system 700.

As shown in FIG. 8A, the insertion of cleaning device 700 into the endotracheal tube can be limited by the sleeve 745 at a compressed state, stopping further movement of the cleaning rod 720 into the tube 10, thereby defining a maximally inserted state. In some embodiments, the external diameter of the sleeve 745 at a compressed state (FIG. 8A) is equal or smaller than the external diameter of the connector outer wall 24, thereby, the sleeve 745 does not limit mounting devices at the connector 20. As shown in FIG. 8A, View B, in some embodiments, the cleaning device 700 comprises one or more buffers 730 mounted on rod 720 in between the cleaning head 750 and the proximal end 724 of the rod, wherein, the external diameter of the buffer 730 is smaller than the diameter of the inner wall of the tube 10. In some embodiments, the buffer 730 is disposed closer to the cleaning head 750 than to the proximal end 724 of the rod 720. The buffer 730 limits the tilting and sideway movements of the rod 720 and/or the cleaning head 750 after inserted within the tube 10 and keeps the rod 720 away of the inside tube wall 13. In some embodiments, the diameter of the buffer 730 is between 3 mm and 8 mm. In some embodiments, the diameter of the buffer 730 is between 5 mm and 6 mm. The buffers can be applied on any of the embodiments of cleaning devices described elsewhere herein (e.g. cleaning devices 100/200/300). As shown in View B, in some embodiments, buffer 730 comprises a plurality of radially extending bars 732, thereby the buffer does not block air passage within the endotracheal tube 10.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:
1. An endotracheal tube cleaning device, comprising:
a rod insertable into an endotracheal tube, and
a cleaning head coupled to a distal end of said rod, comprising:
a discoid base; and
a cleaning layer comprising:
a low friction-generating surface; and
a high friction-generating surface,
wherein said low friction-generating surface contacts an inner surface of said endotracheal tube when moved along said tube in a first direction and said high friction-generating surface contacts the inner surface of said endotracheal tube when moved in a second, opposite direction, wherein said cleaning device is configured to be stowed in said endotracheal tube in between cleanings, at least prior to insertion of said endotracheal tube into a subject or immediately following previous cleaning of said endotracheal tube, and wherein said cleaning layer is configured to deform into a peripheral gap defined between said discoid base and said inner surface of said endotracheal tube, such that upon retraction said cleaning layer bends and pressed against an inner wall of said endotracheal tube.

2. An endotracheal tube cleaning device according to claim 1, wherein said high friction-generating surface comprises a pliable edge and movement of said head within said endotracheal tube in a distal direction flexes said pliable edge proximally bringing said low friction-generating surface to glide along an inner surface of said endotracheal tube.

3. An endotracheal tube cleaning device according to claim 1, wherein movement of said head within said endotracheal tube in a proximal direction flexes at least said pliable edge distally bringing said high friction-generating surface to rub against said inner surface of said endotracheal tube thereby cleaning said inner surface.

4. An endotracheal tube cleaning device according to claim 1, wherein said high friction-generating cleaning surface is textured and said low friction generating surface is smooth.

5. An endotracheal tube cleaning device according to claim 1, wherein a surface area of said low friction generating cleaning surface is smaller than a surface area of said high friction generating surface, wherein said low friction generating surface is located distally to said high friction-generating cleaning surface, wherein said low friction generating surface has a smaller diameter than a diameter of said inner surface of said endotracheal tube defining a gap between an edge of said low friction generating surface and said inner surface sized to accommodate at least a thickness of said low friction generating surface, wherein said cleaning device comprises an insertion limiter coupled to a proximal end of said rod, wherein the diameter of said high friction-generating cleaning surface is equal or larger than the diameter of said inner surface of said endotracheal tube.

6. An endotracheal tube cleaning device according to claim 1, wherein said cleaning device is configured to remain in said endotracheal tube in between cleanings, in a maximally inserted state in which:
at least said rod is disposed within said endotracheal tube;
said cleaning head in a fully inserted state extends beyond a distal rim of the endotracheal tube; and
said insertion limiter engages a proximal rim of the endotracheal tube and blocks further insertion of the device into the tube.

7. An endotracheal tube cleaning device according to claim 1, wherein the cleaning head comprises a proximal high friction-generating cleaning surface, and wherein at a maximally inserted state, said high friction-generating cleaning surface faces said distal rim of the tube and a gap is defined between said high friction-generating cleaning surface and said distal rim of the tube.

8. An endotracheal tube cleaning device according to claim 1, wherein said cleaning device comprises a distal end, and wherein at the maximally inserted state, a gap is defined between a distal end of said cleaning device and patient tissues.

9. An endotracheal tube cleaning device according to claim 1, wherein the diameter of said high friction-generating cleaning surface is equal or larger than the diameter of said inside surface of said endotracheal tube.

10. An endotracheal tube cleaning device according to claim 1, wherein said high friction-generating cleaning surface is configured to flex into a distal eyelet (Murphy's Eye) of said endotracheal tube, when said cleaning head moves in a proximal direction over said eyelet, such as it rubs the surfaces of said eyelet.

11. An endotracheal tube cleaning device according to claim 1, wherein said cleaning device comprises a collector sleeve, configured to receive said cleaning head after being removed from said endotracheal tube.

12. An endotracheal tube cleaning device according to claim 1, wherein said cleaning device comprises one or more rod buffers mounted on said rod in between said distal end and said proximal end of said rod, wherein the external diameter of said buffers is smaller than the diameter of said inner wall of the tube.

13. A method for cleaning an endotracheal tube, comprising:
inserting into a clean endotracheal tube an endotracheal tube device including
a rod insertable into an endotracheal tube, and
a cleaning head coupled to a distal end of said rod, comprising:
a discoid base; and
a cleaning layer comprising:
a high friction-generating surface having at least a pliable edge; and
a low friction-generating surface
an insertion limiter coupled to a proximal end of said rod,
wherein said cleaning layer is configured to deform into a peripheral gap defined between said discoid base and, an inner surface of said endotracheal tube, such that upon retraction said cleaning layer bends and pressed against an inner wall of said endotracheal tube; and
moving said head within said endotracheal tube in a distal direction, and
flexing at least said pliable edge proximally bringing said low friction-generating surface to glide along said inner surface of said endotracheal tube, followed by
retracting said head within said endotracheal tube in a proximal direction; and flexing at least said pliable edge distally bringing said high friction-generating cleaning surface to rub against said inner surface of said endotracheal tube thereby cleaning said inner surface.

14. The method according to claim 13, wherein said method further comprises:
at least partially inserting said cleaning device into a clean endotracheal tube;
inserting said endotracheal tube with said endotracheal tube cleaning device into a trachea; and
inserting said cleaning device further until said insertion limiter abuts a proximal edge of said tracheal tube.

15. The method according to claim 13, wherein said cleaning device comprises a distal end, and wherein inserting said cleaning device until said insertion limiter abuts a proximal edge of said tracheal tube comprises forming a gap between a distal end of said cleaning device and patient tissues.

* * * * *